United States Patent
Nicq

(10) Patent No.: US 10,330,648 B2
(45) Date of Patent: Jun. 25, 2019

(54) METHOD AND DEVICE FOR ACOUSTICALLY DETECTING A MALFUNCTION OF A MOTOR HAVING AN ACTIVE NOISE CONTROL

(71) Applicant: SNECMA, Paris (FR)

(72) Inventor: Geoffroy Nicq, Paris (FR)

(73) Assignee: SAFRAN AIRCRAFT ENGINES, Paris (FR)

( * ) Notice: Subject to any disclaimer, the term of this patent is extended or adjusted under 35 U.S.C. 154(b) by 607 days.

(21) Appl. No.: 14/648,653

(22) PCT Filed: Dec. 12, 2013

(86) PCT No.: PCT/FR2013/053052
§ 371 (c)(1),
(2) Date: May 29, 2015

(87) PCT Pub. No.: WO2014/091165
PCT Pub. Date: Jun. 19, 2014

(65) Prior Publication Data
US 2015/0316512 A1   Nov. 5, 2015

(30) Foreign Application Priority Data

Dec. 13, 2012   (FR) ..................... 12 62025

(51) Int. Cl.
*G01M 15/12* (2006.01)
*G10K 11/178* (2006.01)
*G01N 29/44* (2006.01)

(52) U.S. Cl.
CPC ........ *G01N 29/4436* (2013.01); *G01M 15/12* (2013.01); *G01N 29/4472* (2013.01);
(Continued)

(58) Field of Classification Search
CPC .. G01N 29/44; G10K 11/178; G10K 11/1782; G10K 11/1786; G10K 11/1788; G10L 21/0208
See application file for complete search history.

(56) References Cited

U.S. PATENT DOCUMENTS 5,455,779 A * 10/1995 Sato ............. G10K 11/178
                                                700/280
5,473,244 A * 12/1995 Libove ............ G01R 1/22
                                                324/126
(Continued)

FOREIGN PATENT DOCUMENTS

FR      2 973 877 A1      10/2012

OTHER PUBLICATIONS

Written Opinion of the International Searching Authority dated Mar. 7, 2014, issued in corresponding International Application No. PCT/FR2013/053052, filed Dec. 12, 2013, 8 pages.
(Continued)

*Primary Examiner* — Michael J Dalbo
(74) *Attorney, Agent, or Firm* — Christensen O'Connor Johnson Kindness PLLC

(57) ABSTRACT

The present invention relates to a method for acoustically detecting at least one malfunction (DYS) of a motor, the motor generating a primary noise Po that is treated by an active noise control system emitting, at the noise reduction targets, an acoustic signal Pc produced by at least one actuator and connected by a transfer function H to a signal Y produced by said active noise control system, said malfunction (DYS) having an acoustic signature identifiable in the primary noise Po at the noise reduction targets, characterized in that it comprises the following steps: acquisition of said signal Y produced by the active control system; identification of the appearance, if any, of a malfunction by
(Continued)

Figure 1:
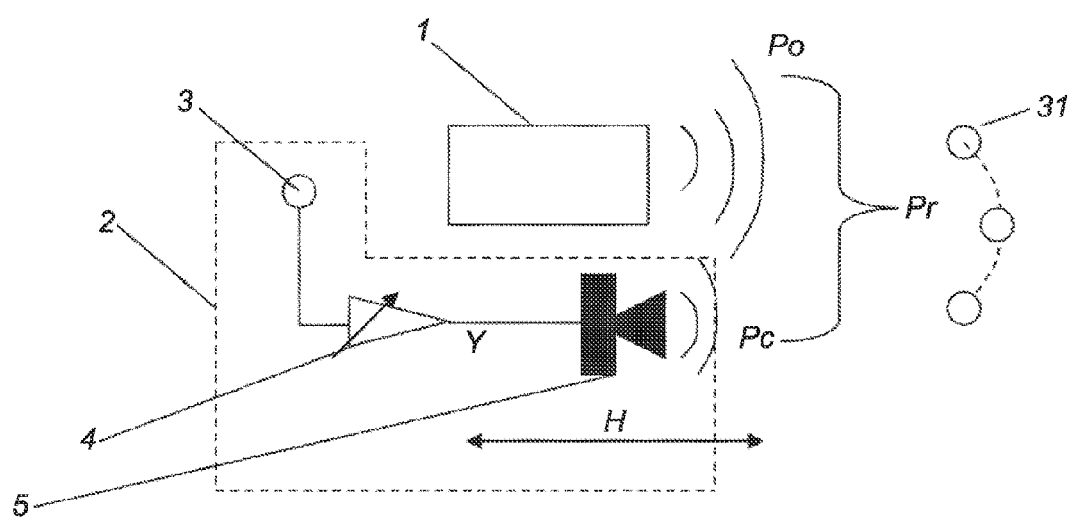

a monitoring means that uses the knowledge of Y and H and emits an alert message if warranted.

12 Claims, 3 Drawing Sheets

(52) U.S. Cl.
CPC ...... *G10K 11/178* (2013.01); *G10K 2210/107* (2013.01); *G10K 2210/1281* (2013.01); *G10K 2210/1282* (2013.01); *G10K 2210/503* (2013.01)

(56) References Cited

U.S. PATENT DOCUMENTS

| | | | | |
|---|---|---|---|---|
| 5,478,199 A * | 12/1995 | Gliebe | .................... | B64D 33/02 415/119 |
| 2004/0258252 A1* | 12/2004 | Inoue | .................... | G10K 11/178 381/71.4 |
| 2008/0142294 A1* | 6/2008 | Cheng | ....................... | F01N 1/02 181/206 |
| 2008/0144849 A1* | 6/2008 | Abe | ...................... | G10K 11/178 381/71.4 |
| 2008/0181422 A1* | 7/2008 | Christoph | .......... | G10K 11/1784 381/73.1 |
| 2009/0086990 A1* | 4/2009 | Christoph | ................ | H04R 3/04 381/71.12 |
| 2009/0136052 A1* | 5/2009 | Hohlfeld | .............. | G10K 11/178 381/71.1 |
| 2010/0111317 A1* | 5/2010 | Asao | .................... | B60R 13/0815 381/71.4 |
| 2010/0203305 A1* | 8/2010 | Takeda | .................... | B60R 13/08 428/219 |
| 2010/0300683 A1* | 12/2010 | Looper | .................... | E21B 21/06 166/250.01 |
| 2011/0150626 A1* | 6/2011 | Kinzie | .................... | G01H 1/003 415/1 |
| 2011/0235693 A1* | 9/2011 | Lee | .......................... | H04S 7/00 375/224 |
| 2012/0189132 A1* | 7/2012 | Sakamoto | ............ | G10K 11/178 381/71.4 |
| 2013/0195282 A1* | 8/2013 | Ohita | .................... | H04R 3/002 381/71.2 |

OTHER PUBLICATIONS

International Preliminary Report on Patentability dated Jun. 16, 2015, issued in corresponding International Application No. PCT/FR2013/053052, filed Dec. 12, 2013, 1 page.
International Search Report dated Mar. 7, 2014, issued in corresponding International Application No. PCT/FR2013/053052, filed Dec. 12, 2013, 2 pages.
Opinion écrite de l'administration chargée de la recherche internationale mailed Mar. 7, 2014, issued in corresponding International Application No. PCT/FR2013/053052, filed Dec. 12, 2013, 7 pages.

* cited by examiner

METHOD AND DEVICE FOR ACOUSTICALLY DETECTING A MALFUNCTION OF A MOTOR HAVING AN ACTIVE NOISE CONTROL

The present invention relates to the field of engines, and in particular to acoustically detecting a malfunction of an engine which is on board an aircraft.

Means for acoustically detecting the malfunction of an engine, for example by identifying the frequency lines which are characteristic of typical faults in its acoustic response to an excitation, are known, as proposed in the patent application EP 1 205 749 for verifying damage to a turbine blade.

Moreover, applying active noise control to aircraft engines, in particular in the example described by the present applicant for acoustically attenuating propeller noise of a turboprop aircraft engine having two contra-rotating propellers in its patent application FR 2 972 710, makes it possible to develop active systems for the acoustic attenuation of the noise of the engine for its environment. Such a system produces an audible signal by means of actuators, such that it is combined with the noise emitted by the engine, referred to here as primary noise, in order to cancel out the perceived noise in target regions of space.

For a device for monitoring engine operation, said active acoustic attenuation systems have the drawback of masking the noises which are characteristic of a malfunction. Knowing that the noises of the malfunctions that are to be monitored have characteristic frequencies, the present applicant has developed a monitoring method consisting in deactivating the active noise control system in narrow frequency bands around these characteristic lines, which method is described in the patent application FR 1153076, filed on 8 Apr. 2011.

This method has several drawbacks. It requires that the harmonics followed by the monitoring device are not reduced in the engine noise. This leads to deterioration in the performance of the active noise attenuation system, since not all the engine harmonics, and the most indicative ones among them, are reduced.

In addition, the control loops of the active control systems are very difficult to develop, and their robustness is critical. In order to minimise the noise and to better identify malfunctions, the frequency ranges in which the noise is not reduced around characteristic lines are limited by inserting narrow band-pass filters into the regulation loop of the active control, thereby leading to significant phase shifts which might destabilise the system. In some configurations, using this method may greatly degrade the noise reduction performance of the active control system, or render it unstable. This problem may be particularly serious if an attempt is made to use the method with an active control system operating in feedback, of which the output data are used to correct the controls of the actuators.

Lastly, when this method is used together with an active control system operating in feedforward, of which the input data are detected upstream without interaction with the noise reduction targets, it requires the use of an additional means for registering noises.

The invention aims to prevent interference with the operation of the active control system, does not impose any performance limitations for noise attenuation and does not introduce, in any case, the use of secondary means for registering noise.

For this purpose, the invention relates to a method for acoustically detecting at least one malfunction (DYS) of an engine, the engine generating a primary noise Po which is processed by an active noise control system which emits, towards the noise reduction targets, an acoustic signal Pc which is produced by at least one actuator and is linked by a transfer function H to a signal Y which is produced by said active noise control system, said malfunction (DYS) having an acoustic signature which can be identified in the primary noise Po at the noise reduction targets, characterised in that it comprises the steps of:

acquiring said signal Y which is produced by the active control system;

identifying the possible occurrence of the malfunction using a monitoring means which utilises the knowledge of Y and of H and emits an alert message if necessary.

Preferably, the signal Y is made up of the set of control signals of the actuators and the monitoring means analyses the primary noise which is reconstructed from the knowledge of Y and of H in order to identify therein the noise of possible malfunctions from characteristic harmonics.

When the transfer function between the signal Y and the noise reduction targets is considered stable and not re-evaluated during operation, a preferred embodiment of the method uses it as a piece of data from the identification step. However, if the transfer function is re-evaluated by the active noise control system, for example owing to a change in engine speed, an embodiment of the method which is adapted to this situation comprises the acquisition of the temporal changes in this transfer function in addition to the signal Y in order to use them in the identification step.

Advantageously, an embodiment of the method limits the calculations in the identification step to characteristic frequencies to be monitored. In this case, an intermediate step between the acquisition and identification extracts reduced indicators on the control signals and the transfer function (the harmonics used for the calculations for reconstructing the primary noise on the characteristic frequencies). The use of reduced indicators greatly reduces the computational load and allows processing in real time using on-board calculation means in the installation comprising the engine.

In an additional variant, the noise control signal and the temporal change in the state of the transfer function are transmitted to the ground for more complete analyses. This makes it possible to further reduce the load on the on-board calculation means.

The invention also relates to a device for acoustically detecting at least one malfunction (DYS) of an engine, the engine generating a primary noise Po, which device is arranged to be used in the presence of an active noise control system which emits, towards the noise reduction targets, an acoustic signal Pc which is produced by at least one actuator and is linked by a transfer function H to a signal Y which is produced by said active noise control system, said malfunction (DYS) having an acoustic signature which can be identified in the primary noise Po at the noise reduction targets, characterised in that it comprises:

a means for acquiring the signal Y which is produced by the active control system;

a monitoring means which is arranged to identify the possible occurrence of the malfunction (DYS) from the signal Y and the knowledge of the transfer function H and to emit an alert message if necessary.

The device for acoustically detecting malfunctions may be adapted to a system for the active reduction of existing noise. It does not require any modification to the control rules or any complementary intrusive instrumentation. If the active noise control system is not equipped with means for reproducing control signals for the purposes of electronic monitoring, simple inductive sensors on the control cables of the actuators may be sufficient for acquiring said signals.

Advantageously, the device is supplemented with means for implementing the various embodiments of the method set out above.

Figure 2:
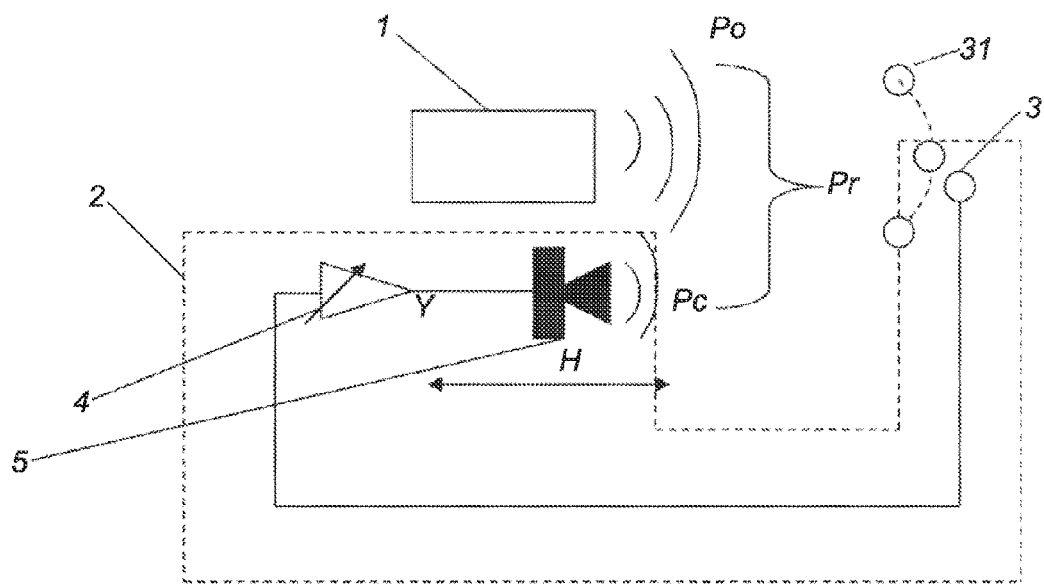
Figure 3:
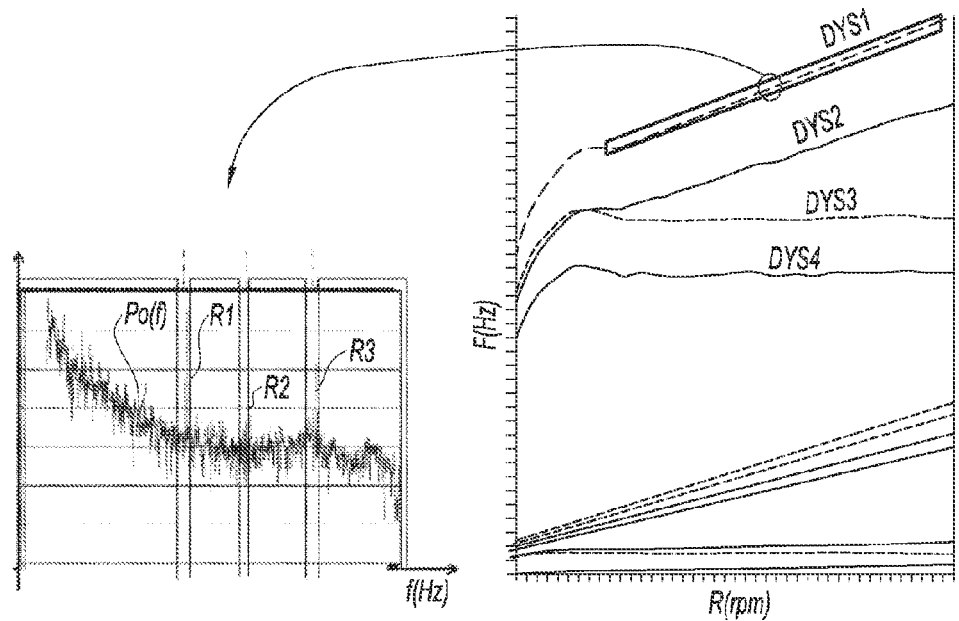
Figure 4:
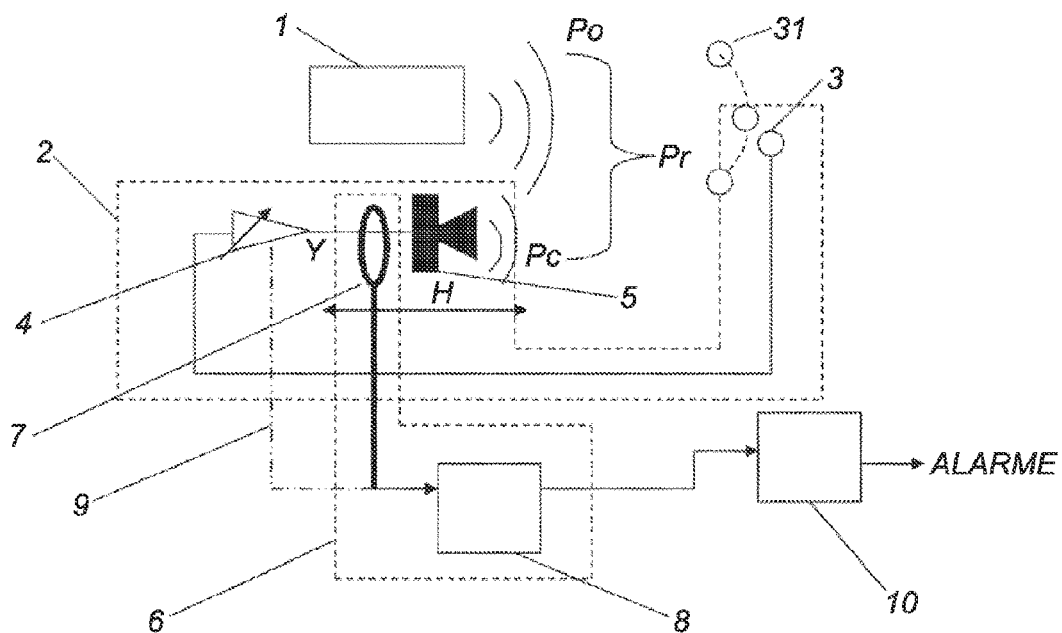
Figure 5:
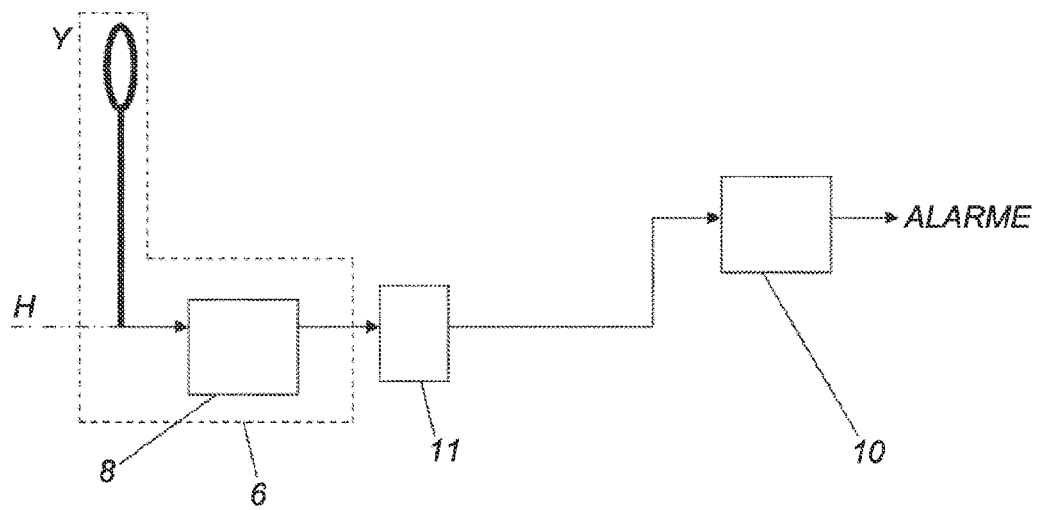
Figure 6:
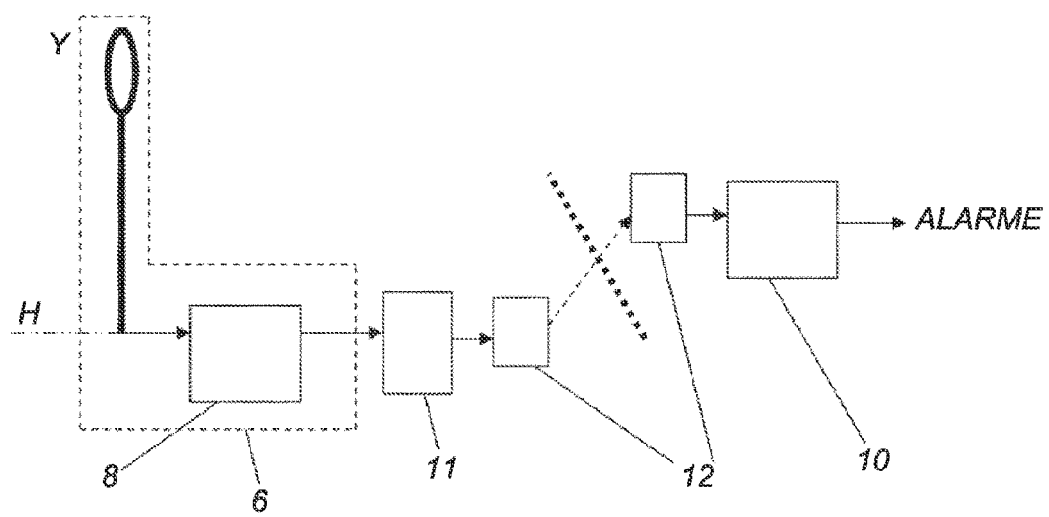

The invention will be better understood on the basis of a more detailed description of an embodiment, with reference to the accompanying drawings, in which:

FIG. 1 schematically shows a method for reducing noise using an active control feedforward system;

FIG. 2 schematically shows a method for reducing noise using an active control feedback system;

FIG. 3 schematically shows the relationship between the characteristic frequency bands of certain malfunctions and the speed of the engine;

FIG. 4 schematically shows the operation of a device for acoustically detecting certain malfunctions of the engine according to the invention in the case of an active control feedback system;

FIG. 5 schematically shows the processing of the information according to a variant of the invention;

FIG. 6 schematically shows the processing of the information according to a second variant of the invention.

FIG. 1 schematically shows the principle of engine-noise reduction in an installation equipped with an active control feedforward system. The installation may be a vehicle, for example an aircraft, or a test rig. The noise reduction targets a region of space that is generally sought to be very extensive. Within this region, the perceived noise is likely to be registered at locations which are referred to as noise reduction targets.

The engine 1 emits a primary noise corresponding to an acoustic signal Po at the noise reduction targets 31. An active noise control system 2 according to the prior art emits, owing to one or more actuators 5, another noise corresponding to a signal Pc at the noise reduction targets, such that the perceived noise Pr remains at an intensity of less than an adequate level by means of the addition of the signals Po and Pc. In order to arrive at this result, the active control system in feedforward mode uses sensors 3 for data on the operation of the engine which do not interfere with the result on the perceived noise Pr, and calculates the control signals sent to the actuators 5 using an algorithm implemented on a computer 4, so that said signals produce the signal Pc towards the noise reduction targets. The signal term Y will be used in the present document to represent all the control signals for the actuators when there is a plurality thereof; the signal Y therefore has a plurality of components in this case.

It may be noted at this point that, by definition, in the frequency band in which the active control system is effective, the perceived noise is low and therefore the noise Pc emitted by the actuators at the noise reduction targets directly gives a good estimation of that of the perceived noise Po by means of a phase shift. In addition, the knowledge of the control signals of the actuators gives direct access to Pc via a transfer function H which takes into account the response of the actuators and the transmission of the acoustic signal therefrom towards the noise reduction targets. Lastly, a good estimation of this transfer function is available since the active noise control system uses it either as input data or by internal evaluation.

A preferred embodiment of the invention therefore uses an evaluation of the primary engine noise at the noise reduction targets by calculating the noise Pc directly from the signal Y produced by the active noise control system by a matrix combination with the transfer function H which may be noted in the frequency domain:

$$Pc_i = Y_k \cdot H_{ki} \qquad (1)$$

Where $Pc_i$ and $Y_k$ are the components of the signals Pc and Y at the frequencies i and k, and $H_{ki}$ is a matrix decomposition of the transfer function H at the calculation frequencies.

FIG. 2 schematically shows the principle of engine-noise reduction in an installation equipped with an active control feedback system. The main difference compared with FIG. 1 is the position of the sensor 3, which, in this case, provides the active control system with information on the perceived noise. This difference is important because it may allow more effective noise reduction systems to be developed, but at the cost of increased complexity of the algorithm used on the computer 4. It is, however, notable that this arrangement does not change the relationship that has been described above between the signals of the actuators and the signal at the noise reduction targets.

FIG. 4 is a basic diagram of a first embodiment of the method according to the invention for acoustically detecting malfunctions of an engine 1 equipped with an active noise control system 2.

A means 6 for acquiring the signal Y preferably uses inductive sensors 7 around control cables of the actuators 5 which are capable of registering this signal. It is generally supplemented with an electronic unit 8 which allows the signal from the sensors to be transformed into a digital signal which can be utilised by the identification means 10.

Acquiring the signal Y is non-intrusive in the sense that it does not have any impact on the operation of the active noise control system 2. If the active control system 2 is equipped with an output providing the signal Y, a simple branch would, for example, constitute a simplified embodiment of the acquisition step.

The signal Y has as many scalar components as there are actuators 5. In the example, Y corresponds to the signal which is sent directly to the actuators, but this is not limiting. For example, a variant of the method uses a signal to an internal component of the active noise control system upstream, of which the transfer function to the actuators is defined.

When the transfer function H between the actuators and the control signals is considered to be stable and not re-evaluated over the course of operation of the active noise control system 2, the algorithm of the monitoring means 10 of the engine which identifies malfunctions emits an alarm signal if necessary, which is supplied solely by the control signals Y of the sensors originating from the acquisition means 6. In a particular embodiment, the primary noise generated by the engine which would be perceived by the noise reduction targets in the absence of active control is reconstructed, according to formula (1), by matrix combination between the control signal Y and the transfer function H, which is a piece of data which is registered on the computer of the monitoring means 10.

In order to carry out the acoustic detection of a malfunction (DYS) in the engine from the reconstructed engine noise, the monitoring means 10 utilises the characteristics of the acoustic signature of said malfunction which may be extracted from this noise. In a manner which is known for engines, each monitored malfunction DYS may be associated with at least one line R1 at a characteristic frequency. The left-hand graph in FIG. 3 shows the manner in which a fault DYS1 may introduce a line R1, and possibly one or more harmonics such as R2 or R3, into the engine noise spectrum at a given speed. Algorithms known to a person skilled in the art make it possible to isolate said lines in the noise spectrum and to associate them with an event to be identified. It is possible, for example, to implement the method used in the patent application FR 1153076, which consists in evaluating the energy intensity in a narrow frequency band around the characteristic line (shown in FIG. 3), and then to identify the signature of the malfunction DYS when a fixed threshold is passed. A person skilled in the art would also know, from these data, to follow the possible occurrence of a plurality of malfunctions corresponding to sets of specific characteristic frequencies. It would also be possible to adapt these algorithms if the characteristic frequencies of said malfunctions change, in particular as a function of the engine speed, as shown on the right-hand graph in FIG. 3. The monitoring means is then equipped with specific algorithms for determining whether or not alarms are triggered as a function of the malfunctions identified.

If the transfer function H changes over time and it is re-evaluated by the computer 4 of the active noise control system of the engine, in a preferred embodiment, the acquisition means 6 receives the information on the changes in the transfer function H, for example by means of a branch 9 leading to the computer 4. In this embodiment, the monitoring means 10 in principle applies the same method of matrix combination of Y and H to each moment, as before, but with a higher volume of calculations than when the transfer function is stable.

The branch 9, contrary to the registration 7 of the control signal Y, may require the active noise control system 2 to be optionally adapted.

FIG. 4 sets out the principle of operation using active noise control system of the feedback type, but the device for acoustically detecting malfunctions would operate in the same manner as for the active noise control system of the feedforward type, since it does not interfere with the operation of the computer 4.

According to an advantageous embodiment, the signal Y, and if necessary changes in the transfer function H, are transformed into frequency components in the acquisition means 6 rather than in the monitoring means 10. This non-limiting arrangement is used in particular for implementing a variant of the method which uses reduced indicators on the signal Y and on the changes in the transfer function.

In this variant, the monitoring means 10 only reconstructs the primary noise on a small number of characteristic frequencies which are sufficient for identifying critical malfunctions. It is therefore only necessary to input information relating to Y and H on a limited number of frequencies in order to reconstruct the noise at the characteristic frequencies. This information is referred to here as the reduced indicators. In a particular embodiment described in FIG. 5, an intermediate means 11 carries out a step of extracting said reduced indicators from the acquisition means 6.

This variant makes it possible to limit the computational power for the means for monitoring engine operation. In order to further limit the computational power required on board the aircraft, for example, a variant of the method consists in moving the means 10 for monitoring malfunctions to the ground. A corresponding embodiment, shown in FIG. 6, includes remote transmission means 12 which are interposed between the extraction means 11 and the remote monitoring means.

Another means for limiting the computational power and for increasing the reliability of the detection is to detect repeatable operational ranges (in 11) and to only implement the harmonic extraction means and the transmission means on the ground during said operating ranges, which are referred to as operating modes.

The invention claimed is:

1. A method for acoustically detecting at least one malfunction of an engine, said method comprising:
processing a primary noise Po generated by said engine by an active noise control system, said active noise control system comprising noise reduction targets receiving in a region the primary noise and configured to identify in said primary noise an acoustic signature corresponding to a malfunction;
emitting an acoustic signal Pc towards said noise reduction targets, said acoustic signal Pc being produced by at least one actuator and linked by a transfer function H to a signal Y for said at least one actuator, said signal Y being produced by said active noise control system;
acquiring said signal Y from an output of the active noise control system by a detector for acoustically detecting at least one malfunction of an engine, wherein said signal Y is acquired using inductive sensors on control cables of the at least one actuator;
identifying the possible occurrence of the malfunction using said detector by utilizing the knowledge of the signal Y and of the transfer function H used by the active noise control system without using a signal being produced by an acoustic sensor; and
emitting an alarm signal when a malfunction is identified.

2. The method according to claim 1, wherein the active noise control system evaluates changes in the transfer function H over time which are the subject of an acquisition and are used by the identification step.

3. The method according to claim 1, wherein the signal Y is formed by a set of control signals of the actuators of the active control system.

4. The method according to claim 1, wherein the detector reconstructs a representation of the acoustic signal Pc by matrix combination between the signal Y and the transfer function H and identifies therein the possible presence of the acoustic signature of said malfunction by comparison with engine noise without any malfunctions.

5. The method according to claim 1, wherein said identifying the possible occurrence of the malfunction is implemented on a limited set of characteristic frequencies, and comprises an intermediate step of extracting signals originating from said acquiring said signal Y which provides indicators reduced to the components Y and H for the frequencies specific to the identification of the malfunction noise at said characteristic frequencies.

6. The method according to claim 1, wherein said step of identifying the possible occurrence of the malfunction is carried out remotely, outside of an installation comprising the engine.

7. The method according to claim 1, wherein the malfunction is identified when the signal Y and/or the transfer function changes over the time.

8. A detector for acoustically detecting at least one malfunction of an engine, the engine generating a primary noise Po, which device is arranged to be used in the presence of an active noise control system which emits, towards noise reduction targets, an acoustic signal Pc which is produced by at least one actuator and is linked by a transfer function H to a control signal Y for said at least one actuator, which signal Y is produced by said active noise control system, said malfunction having an acoustic signature which can be identified in the primary noise Po at the noise reduction targets, the detector comprising:

means for acquiring the signal Y which is produced by the active noise control system wherein the means for acquiring the signal Y comprises inductive sensors on the control cables of the actuators which are capable of receiving the control signals; and monitoring means which is arranged to identify the possible occurrence of the malfunction from the signal Y and the knowledge of the transfer function H used by the active noise control system without using a signal being produced by an acoustic sensor, and to emit an alert message when a malfunction is identified.

9. The device according to claim 8, wherein said means for acquiring the signal Y is arranged to detect, using the active noise control system, changes in the transfer function that it is evaluating over time, and wherein the monitoring means is arranged to use said changes in the transfer function.

10. The device according to claim 8, wherein the device is configured to extract indicators reduced to the components of the signal Y and the transfer function H for the frequencies specific to the identification of the malfunction noise over a limited set of characteristic frequencies.

11. The device according to claim 8, wherein the monitoring means is remote from an installation comprising the engine.

12. A turbine engine capable of generating a primary noise Po, the turbine engine comprising:
  an active noise control system elaborating a transfer function H and a signal Y in order to generate an acoustic signal Pc giving an estimation of the primary noise Po; and
  a detector configured to acoustically detect at least one malfunction of an engine cooperating with the active noise system, said detector being configured to use the transfer function H and the signal Y output by the active noise control system so as to reconstitute the primary noise Po and extract at least a malfunction acoustic signature without using a signal being produced by an acoustic sensor;
  wherein the detector is further configured to acquire said signal Y using inductive sensors on control cables that communicatively couple the active noise control system to at least one actuator for generating the acoustic signal Pc.

\* \* \* \* \*